United States Patent
Inada et al.

(10) Patent No.: US 7,306,738 B2
(45) Date of Patent: Dec. 11, 2007

(54) METHOD OF DEIONIZING SOLUTION YIELDED BY POLYESTER DECOMPOSITION WITH ETHYLENE GLYCOL

(75) Inventors: Shuji Inada, Tokyo (JP); Kikuchi Sato, Fukuyama (JP)

(73) Assignee: Aies Co., Ltd. (JP)

( * ) Notice: Subject to any disclaimer, the term of this patent is extended or adjusted under 35 U.S.C. 154(b) by 107 days.

(21) Appl. No.: 10/477,092

(22) PCT Filed: Dec. 13, 2002

(86) PCT No.: PCT/JP02/13092

§ 371 (c)(1),
(2), (4) Date: Nov. 7, 2003

(87) PCT Pub. No.: WO03/051815

PCT Pub. Date: Jun. 26, 2003

(65) Prior Publication Data

US 2004/0147624 A1 Jul. 29, 2004

(30) Foreign Application Priority Data

Dec. 18, 2001 (JP) .............................. 2001-384555

(51) Int. Cl.
*B01D 15/04* (2006.01)
*C07C 67/56* (2006.01)
*C07C 67/03* (2006.01)
*C07C 69/82* (2006.01)

(52) U.S. Cl. ...................... 210/664; 210/669; 210/683; 521/48.5; 560/78

(58) Field of Classification Search ................ 210/664, 210/669, 685, 683; 521/48, 48.5; 560/78
See application file for complete search history.

(56) References Cited

U.S. PATENT DOCUMENTS

| | | | | |
|---|---|---|---|---|
| 3,896,241 A | * | 7/1975 | Malaspina et al. | 426/271 |
| 4,609,680 A | * | 9/1986 | Fujita et al. | 521/48 |
| 6,630,601 B1 | * | 10/2003 | Inada et al. | 560/76 |
| 6,642,350 B1 | * | 11/2003 | Asakawa et al. | 528/482 |

FOREIGN PATENT DOCUMENTS

| | | |
|---|---|---|
| EP | 0 174 062 A2 | 5/1985 |
| EP | 1 120 394 A1 | 12/1999 |
| WO | WO 01/10812 A1 | 2/2001 |
| WO | WO 01/32597 A1 | 5/2001 |
| WO | WO 01/56970 A1 | 8/2001 |
| WO | WO 02/10117 A1 | 2/2002 |

OTHER PUBLICATIONS

European Search Report which issued in the corresponding European patent application citing above reference.

* cited by examiner

*Primary Examiner*—Fred G. Prince
(74) *Attorney, Agent, or Firm*—Anderson Kill & Olick, PC

(57) ABSTRACT

There is provided a method for deionizing a decomposition produced solution resulting from decomposition of a polyester by ethylene glycol. The ester interchange reaction and hydrolysis reaction along with cation removing treatment of a decomposition product resulting from decomposition of a polyester by ethylene glycol are suppressed. Thereby, a method for deionizing the decomposition produced solution with small reductions in yield and purity can be provided.

15 Claims, No Drawings

METHOD OF DEIONIZING SOLUTION YIELDED BY POLYESTER DECOMPOSITION WITH ETHYLENE GLYCOL

TECHNICAL FIELD

The present invention relates to a method for deionizing a decomposition produced solution resulting from decomposition of a polyester by ethylene glycol. More specifically, the present invention relates to a method for removing ions as impurities from a decomposition produced solution resulting from decomposition of a polyester having a high content of ions as impurities by ethylene glycol, particularly a decomposition produced solution containing, as a main component, bis(2-hydroxyethyl)terephthalate resulting from decomposition of a recovered polyethylene terephthalate by ethylene glycol.

BACKGROUND ART

A polyester, particularly polyethylene terephthalate, is widely used in fields of various molded articles such as a fiber, a film and a resin. The polyethylene terephthalate is generally produced by a method which comprises reacting dimethyl terephthalate or terephthalic acid with ethylene glycol in the presence of a catalyst. At that time, to enable the polyethylene terephthalate to satisfy properties required for a specific application, functional additives such as a stabilizer, a colorant and an antistatic agent are used.

In recent years, disposal of a polyethylene terephthalate molded article, particularly a post-consumer polyethylene terephthalate bottle (PET bottle) is now a social problem in that it pollutes the environment. Accordingly, its collection and recycling are under way.

As one method therefor, a method comprising the steps of collecting a used polyethylene terephthalate molded article, crushing the article into chips or flakes, depolymerizing them with ethylene glycol, purifying the resulting product so as to obtain high-purity bis(2-hydroxyethyl)terephthalate, and then polymerizing the bis(2-hydroxyethyl)terephthalate so as to obtain polyethylene terephthalate is under study.

Based on an idea that in order to obtain a polyester of high quality, a raw material of the polyester must also be of high quality, the present inventor has studied the method comprising the steps of depolymerizing chips or flakes of collected polyethylene terephthalate with ethylene glycol and purifying the resulting product so as to obtain high-purity bis(2-hydroxyethyl)terephthalate. Then, as a finding obtained from the study, the present inventor has proposed a method in which a bis(2-hydroxyethyl)terephthalate solution composition containing ethylene glycol, bis(2-hydroxyethyl)terephthalate and cations and anions as impurities as a solution resulting from the depolymerization reaction is brought into contact with a cation exchanger and an anion exchanger so as to give high-purity bis(2-hydroxyethyl)terephthalate (for example, refer to patent document 1).

Further, as a result of further study on the method, the present inventor has found that since hydrogen ions are liberated by the foregoing cation exchange treatment, a resulting treated solution becomes strongly acidic and bis(2-hydroxyethyl)terephthalate therefore becomes liable to cause an ester interchange reaction with diethylene glycol or a hydrolysis reaction, so that a reduction in yield of the target bis(2-hydroxyethyl)terephthalate or a reduction in purity of the bis(2-hydroxyethyl)terephthalate caused by inclusion of the above reaction products in the bis(2-hydroxyethyl)terephthalate are liable to occur disadvantageously.

(Patent Document 1)

International Publication No. 01/10812 Brochure

An object of the present invention is to provide a method for deionizing a decomposition produced solution resulting from decomposition of a polyester by ethylene glycol, particularly a decomposition produced solution containing, as a main component, bis(2-hydroxyethyl)terephthalate resulting from decomposition of a recovered polyethylene terephthalate by ethylene glycol.

Another object of the present invention is to provide a deionization method in which an ester interchange reaction and hydrolysis reaction of a decomposition product resulting from decomposition of a polyester by ethylene glycol, i.e., bis(2-hydroxyethyl)terephthalate, along with cation removing treatment are suppressed.

Still another object of the present invention is to provide a deionization method in which a reduction in yield and a reduction in purity which are caused by an ester interchange reaction or hydrolysis reaction caused by a decomposition product resulting from decomposition of a polyester by ethylene glycol hardly occur.

Other objects and advantages of the present invention will be apparent from the following description.

DISCLOSURE OF THE INVENTION

According to the present invention, the above objects and advantages of the present invention are achieved by a method for deionizing a decomposition produced solution resulting from decomposition of a polyester by ethylene glycol, the method comprising causing the solution containing a decomposition product, ethylene glycol and cations and anions as impurities to contact with a cation exchanger at a temperature of at most 100° C. for a residence time of 5 to 60 minutes and then with an anion exchanger within 30 minutes immediately thereafter so as to reduce contents of the cations and anions.

A starting material used in the present invention is a decomposition produced solution resulting from decomposition of a polyester by ethylene glycol. The solution contains a decomposition product, ethylene glycol, and cations and anions as impurities. The solution is obtained by decomposing a polyester by an excessive amount of ethylene glycol.

The polyester used in the present invention may be produced by any method. Illustrative examples of the polyester include homopolymers such as a polyethylene terephthalate and polyethylene naphthalate, and copolymers thereof such as copolyesters resulting from copolymerization with isophthalic acid or 1,4-cyclohexane dimethanol and copolyesters resulting from copolymerization with 1,4-butanediol. Of these, the polyethylene terephthalate and copolymers thereof are particularly preferred. For a polyester produced by a polycondensation reaction, glycolysis is generally easy and suitable for the present invention. A solvent used in the glycolysis may contain glycols other than ethylene glycol.

Further, the cations and anions as impurities in the present invention are derived from catalysts for glycolysis (for example, alkali compounds such as sodium hydroxide and potassium hydroxide), catalysts for polymerization of a polyester (for example, antimony compounds such as antimony oxide, germanium compounds such as germanium oxide, and titanium compounds such as titanium alkoxide), and additives such as a stabilizer (such as a phosphorus compound) and an antistatic agent. However, ions originated from a variety of contaminations which are not easily predicted and stuck to or accompanied with the polyester are also included.

The foregoing decomposition produced solution (hereinafter may be referred to as "solution compositions") is brought into contact with a cation exchanger and an anion exchanger. The solution composition can be deionized by, for example, causing the solution composition to pass through layers of the ion exchangers filled in a column or the like so as to make them contact with each other. When the solution composition is a suspension, clogging occurs in the ion exchanger layers, and partial flow are caused by insufficient permeation of the solution composition or permeation resisting spots, so that stable deionization treatment becomes difficult to achieve. Therefore, after solid impurities such as fine particles each having a size of not smaller 1 µm are removed from the solution composition as required, the solution composition must be brought into contact with the cation exchanger and the anion exchanger with the temperature of the solution composition being a temperature which is equal to or lower than maximum usable temperatures of the ion exchange resins and at which crystals of ethylene glycol ester of dicarboxylic acid, particularly bis(2-hydroxyethyl)terephthalate, are not precipitated from a glycolysis reaction solution. It is preferred that the solid impurities having a maximum diameter of not smaller than 1 µm are removed. The removal of solid impurities can be done by a percolation using a diatomite, a fiber filter etc.

In general, the maximum usable temperature of the cation exchanger is higher than that of the anion exchanger. Accordingly, the solution to be treated may be cooled to a temperature equal to or lower than the maximum usable temperature of the anion exchanger after cation exchange treatment or may be subjected to the cation and anion exchange treatments at a temperature equal to or lower than the maximum usable temperature of the anion exchanger. Since the proportion of cations in ion impurities is generally predominantly larger than that of anions, it is preferable to carry out the anion exchange treatment after the cation exchange treatment.

The treated solution becomes acidic due to hydrogen ions generated by the cation exchange treatment. As a result, a decomposition product resulting from decomposition of a polyester by ethylene glycol is liable to cause an ester interchange reaction with coexisting diethylene glycol or a hydrolysis reaction with contained water. Under the circumstances, the present inventor has made intensive studies so as to provide the method for deionizing the decomposition produced solution (solution composition) in which the ester interchange reaction and the hydrolysis reaction are suppressed so as to achieve small reductions in yield and purity. As a result, the present inventor has completed the present invention.

Preferably, firstly, in the present invention, a hydrolysis reaction of a decomposition product resulting from decomposition of a polyester by ethylene glycol is suppressed by reducing the content of water in a glycolysis reaction solution. In general, glycolysis is carried out at a temperature higher than or equal to the boiling point of glycol. Accordingly, when a distillation column is disposed in a glycolysis reactor so as to distill out the water from the reaction solution, the amount of the water in the reaction solution can be reduced so as to suppress the hydrolysis reaction. Meanwhile, evaporated glycol may be put back to the glycolysis reactor.

Preferably, secondly, in the present invention, an ester interchange reaction of the decomposition product resulting from decomposition of the polyester by ethylene glycol is suppressed by shortening residence time of cation exchange treatment. As the temperature at which the ion exchange treatment is carried out increases, a rate of ion exchange also increases. However, since a rate of the ester interchange reaction of the decomposition product also increases along with the above increases, the residence time is shortened so that an amount of the decomposition product converted by the ester interchange reaction does not exceed an acceptable value.

Preferably, thirdly, in the present invention, the ester interchange reaction and hydrolysis reaction of the decomposition product resulting from decomposition of the polyester by ethylene glycol are suppressed by carrying out anion exchange treatment as soon as possible after completion of the cation exchange treatment. Since hydroxide ions are generated by the anion exchange treatment and cause a neutralization reaction with hydrogen ions, hydrogen ions in the reaction solution can be decreased.

Best Mode for Carrying Out the Invention

Hereinafter, the present invention will be described in detail with reference to specific examples. A polyethylene terephthalate is used as the polyester, and glycolysis is carried out by use of ethylene glycol. The temperature of the glycolysis is preferably 160 to 300° C., more preferably 180 to 240° C. The weight ratio between the polyethylene terephthalate and ethylene glycol is preferably 1:9 to 3:7. When the amount of the polyethylene terephthalate is too small with respect to that of ethylene glycol, the amount of bis(2-hydroxyethyl)terephthalate to be produced becomes smaller than saturation solubility to ethylene glycol, so that bis(2-hydroxyethyl)terephthalate can be obtained only in an amount smaller than a maximum yield obtained with respect to the amount of whole solution to be subjected to the deionization treatments, which is not economical. On the other hand, when the amount of the polyethylene terephthalate is too large with respect to that of ethylene glycol, an oligomer of bis(2-hydroxyethyl)terephthalate increases, so that the yield of bis(2-hydroxyethyl)terephthalate decreases. Further, when bis(2-hydroxyethyl)terephthalate exists beyond the saturation solubility to ethylene glycol, bis(2-hydroxyethyl)terephthalate is precipitated, so that the deionization treatments cannot be carried out.

The glycolysis can be carried out by a conventionally known method. Illustrative examples of such a method include a method comprising mixing a molten polyester with ethylene glycol, bis(2-hydroxyethyl)terephthalate or a mixture thereof and depolymerizing the mixture, a method comprising the steps of mixing a molten polyester with ethylene glycol, bis(2-hydroxyethyl)terephthalate, a low degree polymer composition (oligomer) comprising bis(2-hydroxyethyl)terephthalate as a recurring unit, or a mixture thereof so as to pre-depolymerize the mixture and then mixing products resulting from the pre-depolymerization with ethylene glycol so as to depolymerize the mixture, and a method comprising the steps of charging a pulverized polyester and ethylene glycol into a glycolysis reactor and causing them to react with each other. The method using a glycolysis reactor is preferably carried out with a distillation column placed in the glycolysis reactor, while water is removed from a reaction solution to out of the system by distillation. In this case, it is preferable to put evaporated glycol back into the system. By carrying out the glycolysis in such a manner, the amount of water in the solution composition to be brought into contact with a cation exchanger can be reduced, so that a hydrolysis reaction which occurs along with cation removing treatment can be thereby suppressed. It is preferable that the amount of the water contained in the solution composition to be brought into contact with a cation exchanger be adjusted to an amount of not higher than 0.5 wt %.

The reaction solution obtained by the glycolysis contains bis(2-hydroxyethyl)terephthalate as a main component as well as an oligomer of bis(2-hydroxyethyl)terephthalate, diethylene glycol contained in the raw material polyethylene terephthalate, diethylene glycol and 2-hydroxyethyl[2-(2-hydroxyethoxy)ethyl]terephthalate produced from ethylene glycol, and the like. Further, the reaction solution also contains impurity ions derived from a catalyst used in the glycolysis (such as sodium hydroxide), a catalyst used in a polycondensation reaction of the polyethylene terephthalate (such as germanium oxide, antimony oxide, manganese acetate or titanium alkoxide), a stabilizer such as a phosphorus compound, a colorant, and a variety of contaminations which are not easily predicted.

To remove the above impurities from the glycolysis reaction solution, the glycolysis reaction solution is subjected to adsorption treatment using activated carbon so as to remove the colorant and impurities adsorbable to activated carbon and then brought into contact with a cation exchanger and an anion exchanger or the cation exchanger and a mixed layer of the cation exchanger and the anion exchanger. The cation exchanger and the anion exchanger may be particles, chains, fibers or amorphous, for example. When they are in the form of particles, they can be brought into contact with the glycolysis reaction solution by, for example, filling them in a column and causing the glycolysis reaction solution to flow through the column.

As the cation exchanger, a cation exchange resin is preferred, and as the anion exchanger, an anion exchange resin is preferred. Illustrative examples of cation exchange functional groups in the cation exchange resin include —$SO_3H$ and —COOH. Further, as the cation exchange resin, commercial products such as DIAION SK1B, SK104, SK110, SK112 and SK116 (products of Mitsubishi Chemical Corporation) and AMBERLITE IR120B Na, IR120BN Na, IR124 Na and 200CT Na (products of Rohm & Haas Co., Ltd.) can be used. In these commercial products, ion exchange functional groups are generally stabilized as salts such as sodium salts, and they are generally converted into free acid radicals such as those described above upon use of the products.

Illustrative examples of the anion exchange resin include those having anion exchange functional groups such as —$N(CH_3)_2$ and —$NH(C_2H_4NH)_nH$. As these anion exchange resins, commercial products such as DIAION WA10, WA20, WA21J and WA30 (products of Mitsubishi Chemical Corporation) and AMBERLITE IRA67, IRA96SB and XE583 (products of Rohm & Haas Co., Ltd.) can be used. In these commercial products, ion exchange functional groups are generally stabilized as those having not hydroxide ions but halogen anions, and they are generally converted into those having hydroxide ions such as those described above upon use of the products.

Further, gel-type anion exchange resins are classified into a cracked type and a non-cracked type, and the non-cracked type is preferred since it adsorbs a less amount of bis(2-hydroxyethyl)terephthalate. Further, a porous body which is an ion exchange resin having excellent physical durability and a high exchange adsorption rate as compared with the gel-type anion exchange resin, i.e., a so-called MR (microporous) type can also be used.

As for the maximum usable temperature of the cation exchange resin, it is about 120° C. for a strongly acidic styrene resin and about 100° C. for a weakly acidic methacrylic resin. As for the maximum usable temperature of the anion exchange resin, on the other hand, it is about 40 to 60° C. for a strongly basic quaternary ammonium based resin having an —OH type exchange group, about 80° C. or lower for a strongly basic quaternary ammonium based resin having a —Cl type exchange group, and about 100° C. or lower for a weakly basic primary, secondary or tertiary amine (—$NH_2R$, —$NHR_2$, —$NR_3$) type resin. According to the above temperatures, after subjected to the cation exchange treatment at a temperature of, for example, 120° C. or lower, the solution composition can be cooled to a temperature from 40 to 60° C. so as to be subjected to the anion exchange treatment. When bis(2-hydroxyethyl)terephthalate is precipitated due to a decrease in saturation solubility of bis (2-hydroxyethyl)terephthalate caused by a decrease in the temperature, an appropriate amount of ethylene glycol of desired temperature should be added. From an economical standpoint, the anion exchange treatment is desirably carried out by use of a primary, secondary or tertiary amine type anion exchange resin after the cation exchange treatment is carried out preferably at 50 to 100° C., more preferably 60 to 95° C., much more preferably 80 to 90° C.

Illustrative examples of cations in the glycolysis reaction solution include $Na^+$, $Ca^{2+}$, $Mg^{2+}$, $Zn^{2+}$ and $Co^{2+}$ derived from glycolysis catalysts, and $Zn^{2+}$, $Sb^{3+}$, $Ge^{2+}$ and $Ti^{4+}$ derived from polycondensation catalysts. Meanwhile, illustrative examples of anions include $PO_4^{3-}$ derived from a stabilizer and $SO_4^{2-}$ and $Cl^-$ which are ions contaminated to the polyethylene terephthalate. Since the amount of the cations is predominantly larger than that of the anions, it is preferable to carry out the anion exchange treatment after completion of the cation exchange treatment.

Hydrogen ions are generated by the cation exchange reaction as shown by the following formula, and the treated solution becomes acidic.

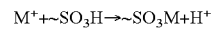

$$M^+ + \sim SO_3H \rightarrow \sim SO_3M + H^+$$

The generated hydrogen ions promote an ester interchange reaction between bis(2-hydroxyethyl)terephthalate produced by glycolysis of the polyethylene terephthalate and diethylene glycol so as to cause 2-hydroxyethyl[2-(2-hydroxyethoxy)ethyl]terephthalate to be by-produced.

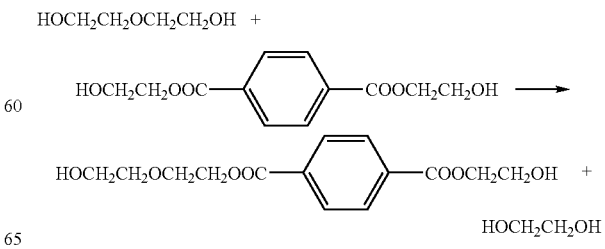

Further, when the treated solution contains a large amount of water, bis(2-hydroxyethyl)terephthalate causes hydrolysis and produces mono(2-hydroxyethyl)terephthalate.

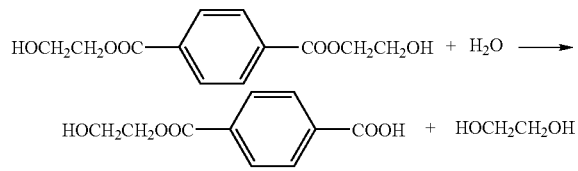

Further, when the solution is treated at high temperatures of, for example, 80 to 90° C., these reactions proceed faster than when the solution is treated at room temperature.

As means for suppressing the ester interchange reaction and hydrolysis reaction of bis(2-hydroxyethyl)terephthalate, a method of neutralizing the hydrogen ions by addition of alkali is conceivable. In this case, since cations derived from the alkali are newly brought to the system, the previously conducted cation removal treatment becomes meaningless undesirably. Further, it is conceivable that the ion exchange treatments are carried out by use of a mixed layer of cations and anions. However, in consideration of regeneration of ion exchange resins arrived in break point, it is preferable to carry out the cation exchange treatment and the anion exchange treatment separately due to a large difference in amount between the cations and the anions.

As a result of intensive studies, the present inventor has found a method of suppressing the above ester interchange reaction and hydrolysis reaction of bis(2-hydroxyethyl) terephthalate by shortening residence time in the cation exchange treatment. The residence time is 5 to 60 minutes, preferably 5 to 50 minutes. When it is shorter than 5 minutes, sufficient cation exchange treatment cannot be carried out, while when it is longer than 60 minutes, an amount of bis(2-hydroxyethyl)terephthalate converted into 2-hydroxyethyl[2-(2-hydroxyethoxy)ethyl]terephthalate by the ester interchange reaction becomes higher than an acceptable value (2.0%). In addition, the present inventor has also found that the above ester interchange reaction and hydrolysis reaction can be suppressed by carrying out the anion exchange treatment as soon as the cation exchange treatment is completed. That is, when hydrogen ions produced by the cation exchange treatment are neutralized with hydroxide ions produced by the anion exchange treatment, free hydrogen ions can be reduced without adding additional alkali to the system, thereby suppressing the ester interchange reaction and the hydrolysis reaction. The anion exchange treatment is carried out within 30 minutes, preferably within 20 minutes, more preferably within 10 minutes after completion of the cation exchange treatment.

The content of ions in an ethylene glycol solution composed essentially of bis(2-hydroxyethyl)terephthalate after the anion exchange treatment is preferably not higher than 2 $\mu$S/cm, more preferably not higher than 1 $\mu$S/cm, in terms of electric conductivity.

EXAMPLES

Hereinafter, a more specific embodiment of the present invention will be described with reference to Examples. It is needless to say that the present invention is not limited to the Examples only. Properties in the Examples were measured in accordance with the following methods.

(Composition of Decomposition Produced Solution)

(Separation of Components and Measurements of Amounts Thereof)

5 mg of sample was dissolved in chloroform so as to prepare about 1,000 ppm of solution. In HPLC model LC-6 of Shimadzu Corporation, measurements were made at a temperature of 40° C., a flow rate of 1.0 ml/min, an injection amount of 5 $\mu$l and a measurement wavelength of 240 nm by use of a Silica-60 column of 4.6 mm$^{ID}$×250 mm$^{L}$, dichloromethane/dioxane as a mobile phase, and a detector of a spectrophotometer for ultraviolet and visible region.

(Identification by LC/MS)

To identify a peak of HPLC, a measurement was carried out by LC/MS. The peak was measured and identified under the same conditions as described above by use of SX-102A manufactured by JEOL.

(Electric Conductivity)

This was measured continuously by means of a process conductivity meter of METTLER TOLEDO CO., LTD.

(Water Content)

This was measured by use of MK-SS type Karl Fischer Moisture Titrator of KYOTO ELECTRONICS MANUFACTURING CO., LTD.

Example 1

(Glycolysis)

76 kg of flakes having an average size of 8 mm×8 mm and prepared by crushing used PET bottles (comprising a polyethylene terephthalate resin) together with 10 wt % of colored PET bottles, 424 kg of industrial grade ethylene glycol, and 230 g of industrial grade sodium hydroxide were charged into a 800-liter autoclave. While the mixture was being stirred at a pressure of 0.13 MPa and a temperature of 215° C., low-boiling-point materials such as water were distilled out from the top of a distillation column disposed in the autoclave, thereby carrying out glycolysis for 110 minutes.

(Removal of Impurities)

The obtained decomposition produced solution was cooled to 180° C. so as to remove solid impurities such as caps and labels contained in the flakes by means of a 60-mesh line strainer, and the resulting solution was transferred to a 800-liter cooling bath. The solution was kept in the cooling bath at 85° C. for 3 hours during which a blue pigment and other insoluble impurities were precipitated. After the precipitated fine particles were removed by means of a 1 $\mu$m cartridge filter, the filtrate was passed through a decolorizing column filled with active carbon for a residence time of 115 minutes.

(Cation Exchange Treatment)

Then, the resulting filtrate was fed into a cation exchange packed column (cation exchange resin: AMBERLITE IR-120B Na, product of Rohm & Haas Co., Ltd.) at 85° C., cation exchange treatment was carried out for a residence time of 12 minutes, and 10 L of the treated solution was then sampled so as to conduct an experiment of a shelf life.

(Anion Exchange Treatment)

Thereafter, the decomposition produced solution was passed through connected piping in 53 seconds, fed into an anion exchange packed column (anion exchange resin: mixture of AMBERLITE IRA96SB and AMBERLITE IR-120B Na, products of Rohm & Haas Co., Ltd.), and subjected to anion exchange treatment at 85° C. The pH of the solution was 5.2 before the cation exchange treatment, 1.76 after the cation exchange treatment, and 4.9 after the anion exchange treatment. Further, the electric conductivity of the solution was 537 µS/cm before the cation exchange treatment and 0.4 µS/cm after the anion exchange treatment.

(Purification)

The above deionized solution was cooled to 25° C. at a cooling rate of 0.5° C./min, crystallized in a crystallizer for 30 minutes, and then subjected to solid-liquid separation, thereby obtaining a wet cake containing 63 wt % of crude bis(2-hydroxyethyl)terephthalate. After the wet cake was molten at 100° C., it was fed into a falling-film type evaporator so as to distill out a low-boiling-point component composed essentially of ethylene glycol at a temperature of 135° C. and a pressure of 513 Pa, thereby concentrating the crude bis(2-hydroxyethyl)terephthalate. Thereafter, the resulting molten cake was fed into a falling-film type molecular still having an internal condenser so as to evaporate the bis(2-hydroxyethyl)terephthalate at a temperature of 208° C., a pressure of 13 Pa and a temperature of the internal condenser of 118° C., and molten bis(2-hydroxyethyl)terephthalate concentrated and purified by the internal condenser was received in a receiver.

Meanwhile, residual components which flew down as the bis(2-hydroxyethyl)terephthalate was caused to evaporate along a heated evaporation surface are extracted from a ring-shaped liquid collection pan disposed underneath the cylindrical evaporation internal surface to the receiver in a molten state.

(Shelf Life of Solution Subjected to Cation Exchange Treatment)

5 L of the solution after the cation exchange treatment was kept at 85° C., and a proportion of 2-hydroxyethyl[2-(2-hydroxyethoxy)ethyl]terephthalate converted from bis(2-hydroxyethyl)terephthalate in the whole solution was measured on a weight basis upon passages of 10, 20, 40, 60 and 120 minutes. As a result, it was initially 2.8% and then increased to 3.1%, 3.5%, 4.0%, 5.1% and 6.6% successively. Thereby, it was confirmed that the anion exchange treatment must be carried out as soon as the cation exchange treatment was completed.

Example 2

Purified bis(2-hydroxyethyl)terephthalate was obtained in the same manner as in Example 1 except that the residence time in the cation exchange treatment was changed to 30 minutes. The results are shown in Table 1.

Example 3

Purified bis(2-hydroxyethyl)terephthalate was obtained in the same manner as in Example 1 except that the residence time in the cation exchange treatment was changed to 60 minutes. The results are shown in Table 1.

In addition, 5 wt % of water was added to the solution subjected to the cation exchange treatment, and a proportion of mono(2-hydroxyethyl)terephthalate converted from bis (2-hydroxyethyl)terephthalate in the whole solution was measured on a weight basis upon passages of 10, 20, 40, 60 and 120 minutes. As a result, it was 2.5% before the addition of water and then increased to 3.0%, 3.6%, 4.0%, 5.7% and 9.1% successively. Thereby, it was confirmed that mono(2-hydroxyethyl)terephthalate increased with passage of time.

Comparative Example 1

Example 1 was repeated except that the anion exchange treatment was not carried out. As a result, distill-out of bis(2-hydroxyethyl)terephthalate was not seen at all at the time of molecular distillation, and a highly viscous, light-yellow substance (melting point: 63° C.) was obtained instead. As a result of analyzing the substance, it was an oligomer mixture containing 73.2 wt % of 2-hydroxyethyl [2-(2-hydroxyethoxy)ethyl]terephthalate. It was thereby confirmed that both the cation exchange treatment and the anion exchange treatment were essential.

Comparative Example 2

Purified bis(2-hydroxyethyl)terephthalate was obtained in the same manner as in Example 1 except that the residence time in the cation exchange treatment was 2 hours and the residence time in the connected piping was 5 minutes. The results are shown in Table 1.

Comparative Example 3

Purified bis(2-hydroxyethyl)terephthalate was obtained in the same manner as in Example 1 except that the solution subjected to the cation exchange treatment was reserved in a tank once and the solution was then subjected to the anion exchange treatment after passage of 60 minutes. The results are shown in Table 1.

Comparative Example 4

Purified bis(2-hydroxyethyl)terephthalate was obtained in the same manner as in Example 1 except that the residence time in the cation exchange treatment was 3 minutes. In this case, the electric conductivity of a solution was 537 µS/cm before the cation exchange treatment and 12 µS/cm after the anion exchange treatment. In subsequent molecular distillation, distill-out of the purified bis(2-hydroxyethyl)terephthalate was little, and distill-out of oligomer was increased instead. It was thereby confirmed that when the cation exchange treatment is insufficient, residual cations serving as a catalyst promote conversion of bis(2-hydroxyethyl) terephthalate into an oligomer.

Table 1 shows proportions of 2-hydroxyethyl[2-(2-hydroxyethoxy)ethyl]terephthalate converted from bis(2-hydroxyethyl)terephthalate in the whole solutions in Examples 1 to 3 and Comparative Examples 2 and 3. Optical densities in Table 1 are used to evaluate the quality of bis(2-hydroxyethyl)terephthalate and are values considered to be proportional to the content of colorant. More specifically, they are values resulting from measuring the absorbance of 10-wt % methanol solution of bis(2-hydroxyethyl)terephthalate at a cell length of 10 mm and a wavelength of 380 nm.

TABLE 1

|  | Ex. 1 | Ex. 2 | Ex. 3 | C. Ex. 2 | C. Ex. 3 |
|---|---|---|---|---|---|
| Time from Start of Cation Exchange Treatment to Start of Anion | 12.9 | 30.9 | 60.9 | 125 | 180 |

TABLE 1-continued

|  | Ex. 1 | Ex. 2 | Ex. 3 | C. Ex. 2 | C. Ex. 3 |
|---|---|---|---|---|---|
| Exchange Treatment (minute) 2-hydroxyethyl[2-(2-hydroxyethoxy)ethyl]terephthalate (wt %) | | | | | |
| In Solid Content Before Cation Exchange | 1.31 | 1.31 | 1.32 | 1.30 | 1.31 |
| In Solid Content After Cation Exchange | 2.63 | 2.69 | 3.80 | 11.41 | 11.37 |
| In Cake Resulting from Crystallization and Solid-Liquid Separation | 1.72 | 1.98 | 2.39 | 6.68 | 16.66 |
| In Purified bis(2-hydroxyethyl)terephthalate | 1.41 | 1.60 | 1.93 | 3.92 | 9.78 |
| Optical Density of Purified bis(2-hydroxyethyl)terephthalate | 0.000 | 0.001 | 0.002 | 0.077 | 0.154 |

Ex.: Example,
C. Ex.: Comparative Example

EFFECTS OF THE INVENTION

As described above, according to the method of the present invention for deionizing a decomposition produced solution resulting from decomposition of a polyester by ethylene glycol, the ester interchange reaction and hydrolysis reaction of the decomposition product along with cation removing treatment can be suppressed. Consequently, a method for deionizing the above decomposition produced solution with small reductions in yield and purity can be provided.

The invention claimed is:

1. A method for deionizing a decomposition produced solution having a water content of not higher than 0.5 wt % resulting from decomposition of a polyester by ethylene glycol, with the weight ratio between the polyester and ethylene glycol of 1:9 to 3:7, wherein during decomposition water is distilled out of the solution and evaporated ethylene glycol is returned into the solution, the method further comprising:

bringing the solution containing a decomposition product, ethylene glycol and cations and anions as impurities into contact with a cation exchanger at a temperature of not higher than 100° C. for a residence time of 5 to 60 minutes and then with an anion exchanger within 10 minutes after the contact with the cation exchanger so as to reduce contents of the cations and anions.

2. The method of claim 1, wherein the anion exchanger consists of a mixed layer of the cation exchanger and the anion exchanger.

3. The method of claim 2, wherein a decomposition produced solution prepared by decomposing a polyester by ethylene glycol while water is distilled out is used.

4. The method of claim 2, wherein solid impurities each of which is not smaller than 1 μm are removed from the decomposition produced solution before the solution is brought into contact with the cation exchanger and the anion exchanger.

5. The method of claim 2, wherein the polyester is polyethylene terephthalate.

6. The method of claim 2, wherein the electric conductivity of decomposition produced solution after the anion exchange treatment is not higher than 1 μS/cm.

7. The method of claim 1, wherein solid impurities each of which is not smaller than 1 μm are removed from the decomposition produced solution before the solution is brought into contact with the cation exchanger and the anion exchanger.

8. The method of claim 7, wherein the polyester is polyethylene terephthalate.

9. The method of claim 7, wherein the electric conductivity of decomposition produced solution after the anion exchange treatment is not higher than 1 μS/cm.

10. The method of claim 1, wherein the polyester is polyethylene terephthalate.

11. The method of claim 10, wherein the electric conductivity of decomposition produced solution after the anion exchange treatment is not higher than 1 μS/cm.

12. The method of claim 1, wherein the electric conductivity of decomposition produced solution after the anion exchange treatment is not higher than 1 μS/cm.

13. The method of claim 1, wherein solid impurities each of which is not smaller than 1 μm are removed from the decomposition produced solution before the solution is brought into contact with the cation exchanger and the anion exchanger.

14. The method of claim 1, wherein the polyester is polyethylene terephthalate.

15. The method of claim 1, wherein the electric conductivity of decomposition produced solution after the anion exchange treatment is not higher than 1 μS/cm.

* * * * *

UNITED STATES PATENT AND TRADEMARK OFFICE
CERTIFICATE OF CORRECTION

PATENT NO. : 7,306,738 B2　　　　　　　　　　　　　　　　　　　　　　　Page 1 of 1
APPLICATION NO. : 10/477092
DATED : December 11, 2007
INVENTOR(S) : Shuji Inada and Kikuchi Sato It is certified that error appears in the above-identified patent and that said Letters Patent is hereby corrected as shown below:

On the Title Page Item (73)
Please correct the name of the assignee as follows:

PET REBIRTH CO., LTD.

Signed and Sealed this

Eighteenth Day of November, 2008

JON W. DUDAS
*Director of the United States Patent and Trademark Office*